United States Patent [19]

Daniel

[11] Patent Number: 5,457,100
[45] Date of Patent: Oct. 10, 1995

[54] METHOD FOR TREATMENT OF RECURRENT PAROXYSMAL NEUROPSYCHIATRIC

[76] Inventor: David G. Daniel, 6408-P Seven Corners Pl., Falls Church, Va. 22044

[21] Appl. No.: 79,968

[22] Filed: Jun. 3, 1993

Related U.S. Application Data

[63] Continuation of Ser. No. 801,491, Dec. 2, 1991, abandoned.

[51] Int. Cl.$^6$ .................. A61K 31/55; A61K 31/495; A61K 31/44; A61K 31/135
[52] U.S. Cl. .................. 514/220; 514/255; 514/294; 514/651; 514/958
[58] Field of Search .................. 514/220, 650, 514/651, 958, 255, 294; 424/43, 44, 45

[56] References Cited

U.S. PATENT DOCUMENTS

| | | | |
|---|---|---|---|
| 4,510,153 | 4/1985 | Coleman | 514/220 |
| 4,634,703 | 1/1987 | Kurtz et al. | 514/252 |
| 4,782,060 | 11/1988 | Kurtz et al. | 514/252 |
| 4,783,477 | 11/1988 | Lammintausta et al. | 514/396 |
| 4,814,161 | 3/1989 | Jinks et al. | 424/45 |
| 4,895,719 | 1/1990 | Radhakrishnan et al. | 424/45 |
| 4,962,128 | 10/1990 | Doogan et al. | 514/647 |
| 4,980,354 | 12/1990 | Cairns et al. | 514/255 |
| 5,118,494 | 6/1992 | Schultz et al. | 424/45 |
| 5,166,202 | 11/1992 | Schweizer | 514/220 |

FOREIGN PATENT DOCUMENTS 3326089  2/1985  Germany.

OTHER PUBLICATIONS

Practical Pharmacy Edition, vol. 19, No. 11, Nov. 1958 "Aerosol Dosage Forms" Bau.

*Primary Examiner*—Raymond Henley, III
*Attorney, Agent, or Firm*—Mary Helen Sears

[57] ABSTRACT

Recurrent paroxysmal neuropsychiatric disorders selected from (1) acute dystonic reactions, (2) seizure disorders and (3) panic disorders may be treated by means of aerosol inhalation of (1) anticholinergic and/or antihistaminic agents, (2) benzodiazepines and (3) antihistaminic agents, respectively.

**11 Cla

METHOD FOR TREATMENT OF RECURRENT PAROXYSMAL NEUROPSYCHIATRIC

This is a continuation of application Ser. No. 07/801,491, filed on Dec. 2, 1991, now abandoned.

This invention relates to methods for the treatment of recurrent paroxysmal neuropsychiatric disorders of rapid onset and brief duration, such as acute dystonic reactions, seizure disorder and panic disorder.

Acute Dystonic Reactions are a common, frightening, extremely uncomfortable and potentially fatal side effect of neuroleptic medications. These reactions are characterized by acute muscular rigidity and cramping (sometimes of sufficient severity to dislocate joints, obscure vision, or to obstruct the airway). Neuroleptic medications are widely used throughout the world and are the mainstay of pharmacologic treatment of schizophrenia, mood disorders with psychotic components, Tourette's syndrome, agitated, explosive behavior, intractable hiccups, and intractable vomiting. Of patients taking neuroleptic medication, 11.9% will experience acute dystonic reactions.

Panic Disorder is a psychiatric syndrome characterized by extreme anxiety or terror which is accompanied by severe muscle tension and autonomic hyperactivity. It occurs in discrete episodes of abrupt onset ("panic attacks") and is a recurrent condition.

Seizure disorders may be of the generalized tonic clonic (grand mal), partial motor, or psychomotor type. Generalized convulsive seizures are characterized by violent involuntary contractions of the muscles. Prolonged seizures (status epilepticus) may damage cerebral tissue. In approximately half of cases generalized convulsive seizures are preceded by a warning sensation called an "aura" that may be recognized by the patient or his family. Focal seizures may begin in an extremity while the patient is awake and alert and may progress over a matter of seconds or minutes to full blown generalized convulsion (Jacksonian March).

While the causes of these three conditions are different, their symptoms have in common an abrupt onset with rapid escalation of symptoms and a relatively brief duration. Each disorder may be preceded by brief warning symptoms (an "aura") before the rapid escalation of symptoms begins. Consequently, their symptomatic treatment may in both cases benefit from an agent with extremely rapid onset.

Some agents have been shown to be effective in the prevention of recurring panic disorder attacks. Examples of this are reported in U.S. Pat. No. 4,980,354, Cairns, et al.; U.S. Pat. No. 4,962,128, Doogan, et al.; U.S. Pat. No. 4,783,477, Lammintausta et al.; U.S. Pat. No. 4,782,060, Kurtz et al.; U.S. Pat. No. 4,634,703, Kurtz et al.; U.S. Pat. No. 4,510,153 Coleman. They are administered orally, by injection, or by ingestion so as to maintain in the patient's body a therapeutic drug concentration which lessens the frequency of these events. However, such techniques do not completely eliminate their occurrence. Moreover, long term prophylactic use of such agents exposes the patient to a high risk of physical and psychological withdrawal symptoms following discontinuance of long-term use.

Currently, the only effective way to interrupt an acute dystonic reaction is to administer an intramuscular or an intravenous injection of diphenhydramine or an anticholinergic agent such as benztropine or biperiden. This normally requires the patient, if not currently hospitalized, to be taken to a hospital emergency room. A substantial delay usually occurs after onset of symptoms before medication can be injected because time is lost calling for help (if the patient can speak) being transported to the hospital, being checked into the hospital, and being evaluated. During this lapse between onset of symptoms and initiation of treatment the patient may experience extreme discomfort and interference in breathing, swallowing and speaking.

The most effective pharmacological means of aborting a panic attack is an intramuscular or intravenous injection of a benzodiazepine or antihistamine. This also normally requires the patient to be taken to a hospital emergency room. Again, a substantial period of time usually elapses after onset of symptoms before medication can be injected because time is lost attaining assistance, being transported to the hospital, being checked into the hospital, and being evaluated. During this lapse between onset of symptoms and initiation of treatment, the patient may experience terrifying anxiety and severe physical discomfort.

The only currently available means of interrupting a seizure or preventing a seizure once a warning aura has appeared is an injection of a benzodiazepine.

These methods of treatment are not entirely satisfactory. Oral administration of drugs does not result in a rapid response and it is inadvisable if the patient has difficulty swallowing (as is often the case). It is very difficult to administer an injection to someone who has fallen into uncontrollable, perhaps violent motor activity. Also, failure to terminate an attack in its early stages risks physical and emotional harm to the patient and the patient's family.

Accordingly, it is desired to provide a method of treating acute panic disorder and acute dystonic reaction which is fast acting, can be administered by the patient and which can terminate the event before its symptoms become severe.

According to the present invention, this is achieved by administering an effective dose of a therapeutic agent by aerosol inhalation. This may be done by the patient, without assistance, at the first sign of an attack, or aura. By this technique, the therapeutic agent can be applied to the respiratory mucosa which is highly vascularized and permeable to these agents. Prompt intervention in this manner allows the rapid absorption and action of these drugs and the early termination of the event, sometimes even before its symptoms become serious.

Panic attacks can be treated in this manner by administering antihistamines such as diphenhydramine and hydroxyzine.

Acute dystonic reactions are advantageously treated by administering antihistamines or anticholinergics (such as benztropine, biperiden or trihexyphenidyl). Benztropine and diphenhydramine are generally preferred.

Seizures may be interrupted at the first sign of an aura or after the full seizure begins by administering benzodiazepines such as diazepam or lorazepam. Diazepam is preferred.

The method of the present invention may be practiced in the following manner:

A pharmaceutical grade of a suitable benzodiazepine, antihistamine, or anticholinergic active ingredient can be dissolved in a non-toxic solubilizing substance, such as ethyl alcohol in sufficient proportion to maintain the solubility of the active ingredient in the propellant.

Appropriate adjuvants may be added to improve absorption through the nasal or pulmonary mucosa. Compounds reported to be effective for this purpose include surfactants such as sodium glycocholate, saponin, polyoxyethylene-9-laurylether and sodium taurodihydrofusidate. Compounds suitable for use as propellants in aerosolized medical preparations include ethyl chloride, butane, propane, dichlorodifluoromethane, dichlorotetrafluoroethane, and trichloromonofluoromethane.

A suitable vapor pressure for such a device is between 15 and 60 pounds per square inch at room temperature (20–25 degrees centigrade).

There are three commonly used and effective means of delivering medication into the lungs or nasal cavity: 1) aerosolized metered dose pumps, 2) manual metered dose pumps, and 3) metered dose spray-producing squeeze bottles. Each of these is effective in providing for the rapid absorption of medicinal compounds into the blood stream. The choice of delivery system will depend on the preference or physical limitations of the individual patient. In unconscious patients experiencing seizures, however, the aerosolized metered dose pump connected to a close fitting plastic mask covering the nose and mouth (such as is commonly used to administer oxygen) is the most effective delivery system.

The propellant is combined with the mixture of active ingredient dissolved in the ethyl alcohol (or other suitable solubilizing substance) and surfactant or other absorption-enhancing compound in an aerosol canister containing a metered valve suitable for delivering a single predetermined volume. Aerosol containers such as this may be composed of any non-toxic substance capable of withstanding sufficient internal pressure and are widely utilized commercially. They generally operate by filling a well of predetermined volume with the self-propelling composition which is dispersed as an aerosol. The substance mixtures and propellant may be mixed before they are placed into the aerosol canister or placed into the canister separately, by commercially available pressure or cold-filled methods. When the canister is depressed, a mouthpiece or nasal adapter will deliver a predetermined volume of the contents, containing a predetermined dosage of the active ingredient into the pulmonary or nasal cavity, respectively as the patient takes a deep inhalation.

Appropriate predetermined dosages to be delivered with each actuation are described below. These dosages are based on Food and Drug Administration recommendations for parenteral or oral use of these medications.

Illustrative Examples of Formulations Useful for Interruption of Panic Attacks

Example A:

20% diphenhydramine
20% anhydrous ethanol
25% dichlorodifluoromethane
25% trichloromonofluoromethane
12.5 mg. diphenhydramine is delivered per actuation Example B:

20% hydroxyzine
30% anhydrous ethanol
25% dichlorodifluoromethane
25% trichloromonofluoromethane
12.5 mg. hydroxyzine is delivered by actuation Illustrative Examples of Formulations Useful for Interruption of Acute Dystonic Reactions Example A:

05% benztropine
25% anhydrous ethanol

-continued

35% dichlorodifluoromethane
35% trichloromonofluoromethane
2.0 mg. benztropine is delivered per actuation Example B:

05% trihexyphenidyl
25% anhydrous ethanol
35% dichlorodifluoromethane
35% trichloromonofluoromethane
2.0 mg. trihexyphenidyl is delivered per actuation Example C:

05% biperiden
25% anhydrous ethanol
35% dichlorodifluoromethane
35% trichloromonofluoromethane
2 mg. biperiden delivered per actuation Example D:

20% diphenhydramine
30% anhydrous ethanol
25% dichlorodifluoromethane
25% trichloromonofluoromethane
12.5 mg. diphenhydramine is delivered per actuation Illustrative Examples of Formulations Useful for Interruption of Seizures Example A:

25% diazepam
35% anhydrous ethanol
20% dichlorodifluoromethane
20% trichloromonofluoromethane
5.0 mg. diazepam delivered per actuation Example B:

05% lorazepam
25% anhydrous ethanol
35% dichlorodifluoromethane
35% trichloromonofluoromethane
1.0 mg. lorazepam delivered per actuation Example C:

05% clonazepam
25% anhydrous ethanol
35% dichlorodifluoromethane
35% trichloromonofluoromethane
0.5 mg. clonazepam delivered per actuation The mixture of active ingredient dissolved in ethyl alcohol (or other suitable solubilizing substance) and surfactant (or other absorption-enhancing compounds) can be placed in a pump canister containing a metered valve suitable for delivering a single predetermined volume. Canisters such as this may be composed of any non-toxic substance capable of withstanding sufficient internal pressure and are widely utilized commercially. They generally operate by filling a well of predetermined volume with the composition which is dispersed as a suspension by depressing the manual pump. To operate the manual pump spray unit, the pump if first primed by depressing the pump several times. Subsequently, when the pump is depressed the mouthpiece adapter or nasal adapter will deliver a predetermined volume of the contents, containing a predetermined concentration and dosage of the "active ingredient" into the lungs or nasal cavity as the patient takes a deep inhalation. Appropriate predetermined dosages of active ingredient to be delivered with each actuation are identical to those described for the aerosolized metered dose pump.

The mixture of active ingredient dissolved in ethyl alcohol (or other suitable solubilizing substance) and surfactant (or other absorption-enhancing compound) can be placed in a flexible squeeze bottle suitable for delivering a single predetermined volume. Squeeze bottles such as this may be composed of any flexible non-toxic substance such as plastic that is capable of withstanding sufficient internal pressure and are widely utilized commercially. When the squeeze bottle is squeezed the mouthpiece or nasal adapter will deliver a predetermined volume of the contents, containing a predetermined concentration and dosage of the "active ingredient" into the nasal cavity as the patient takes a deep inhalation. Appropriate predetermined dosages of active ingredient to be delivered with each actuation are identical to those described for the aerosolized metered dose pump.

I claim:

1. A process for the treatment of recurrent paroxysmal neuropsychiatric disorders of brief duration selected from acute dystonic reaction and seizure disorder which comprises the step of administering to a patient who has experienced symptoms that indicate an episode of the disorder is about to occur and before onset of the episode, by means of aerosol inhalation, an efficacious dose of a therapeutic agent which, (i) for acute dystonic reaction is selected from anticholinergics and antihistamines, and (ii) for seizure disorder is a benzodiazepine.

2. The process of claim 1, wherein the episode is acute dystonic reaction and the therapeutic agent is selected from the group consisting of at least about 2.0 mg of benztropine and at least about 12.5 mg of diphenhydramine.

3. The process of claim 1, wherein the episode is seizure disorder and the therapeutic agent is at least about 5.0 mg of diazepam.

4. The process of claim 1, wherein the therapeutic agent is administered by aerosol inhalation through the nose.

5. The process of claim 1, wherein the therapeutic agent is administered by aerosol inhalation through the mouth.

6. A process for the treatment of recurrent paroxysmal neuropsychiatric disorders of brief duration selected from among panic disorder, acute dystonic disorder and seizure disorder which comprises the step of administering to a patient who is experiencing symptoms of such disorder, by means of aerosol inhalation, an efficacious dose of a therapeutic agent which (i) for acute panic disorder is an antihistamine, (ii) for acute dystonic reaction is selected from anticholinergics and antihistamines, (iii) for seizure disorder is a benzodiazepine.

7. The process of claim 6, wherein the episode is acute dystonic reaction and the therapeutic agent is selected from the group consisting of at least about 2.0 mg of benztropine and at least about 12.5 mg of diphenhydramine.

8. The process of claim 6, wherein the episode is panic disorder and the therapeutic agent is selected from the group consisting of at least about 12.5 mg of diphenhydramine and at least about 12.5 mg of hydroxyzine.

9. The process of claim 6, wherein the episode is seizure disorder and the therapeutic agent is at least about 5.0 mg of diazepam.

10. The process of claim 6, wherein the therapeutic agent is administered by aerosol inhalation through the nose.

11. The process of claim 6, wherein the therapeutic agent is administered by aerosol inhalation through the mouth.

* * * * *